(12) United States Patent
Lennox et al.

(10) Patent No.: US 7,547,291 B2
(45) Date of Patent: *Jun. 16, 2009

(54) TREATING URINARY RETENTION

(75) Inventors: Charles D. Lennox, Hudson, NH (US); Ronald B. Lamport, Pelham, NH (US); Andrew H. Levine, Newton Center, MA (US); Douglas E. Godshall, Franklin, MA (US); Aaron Perlmutter, New York, NY (US); Steven Nordstrom, Franklin, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 556 days.

This patent is subject to a terminal disclaimer.

(21) Appl. No.: 11/018,836

(22) Filed: Dec. 21, 2004

(65) Prior Publication Data

US 2005/0107735 A1 May 19, 2005

Related U.S. Application Data

(63) Continuation of application No. 10/260,483, filed on Sep. 30, 2002, now Pat. No. 6,835,183, which is a continuation of application No. 09/313,563, filed on May 14, 1999, now Pat. No. 6,494,879.

(60) Provisional application No. 60/104,390, filed on Oct. 15, 1998.

(51) Int. Cl.
*A61M 5/00* (2006.01)
*A61F 2/04* (2006.01)

(52) U.S. Cl. ........................ 604/8; 623/23.66

(58) Field of Classification Search ............... 604/8, 604/9; 623/23.66
See application file for complete search history.

(56) References Cited

U.S. PATENT DOCUMENTS

| 3,731,670 | A | 5/1973 | Loe |
| 3,923,066 | A | 12/1975 | Francisoud et al. |
| 4,284,081 | A | 8/1981 | Kasper et al. |
| 4,307,723 | A | 12/1981 | Finney |
| 4,350,161 | A | 9/1982 | Davis, Jr. |
| 4,432,757 | A | 2/1984 | Davis, Jr. |
| 4,501,580 | A | 2/1985 | Glassman |
| 4,655,771 | A | 4/1987 | Wallsten |
| 4,713,049 | A | 12/1987 | Carter |

(Continued)

FOREIGN PATENT DOCUMENTS

DE 295 07 519 U1 9/1995

(Continued)

OTHER PUBLICATIONS

"An overview of superelastic stent design" T.W. Deurig et al.—Minimally Invasive Therapy & Allied Technologies- vol. 9, No. (3/4), Aug. 2000, ISSN 1364-5706—pp. 235-246.

(Continued)

*Primary Examiner*—Bruce E Snow
(74) *Attorney, Agent, or Firm*—Cooley Godward Kronish LLP

(57) ABSTRACT

A urethral prosthesis provides relief of urinary retention and has first and second tubular elements with an interposed bridge segment. A valve can be disposed in the second tubular element to control the flow of urine therethrough.

38 Claims, 10 Drawing Sheets

U.S. PATENT DOCUMENTS

| | | | |
|---|---|---|---|
| 4,732,152 A | 3/1988 | Wallsten et al. | |
| 4,762,128 A | 8/1988 | Rosenbluth | |
| 4,813,429 A | 3/1989 | Eshel et al. | |
| 4,813,935 A | 3/1989 | Haber et al. | |
| 4,893,623 A | 1/1990 | Rosenbluth | |
| 4,931,037 A | 6/1990 | Wetterman | |
| 4,932,938 A * | 6/1990 | Goldberg et al. | 604/99.04 |
| 4,932,956 A | 6/1990 | Reddy et al. | |
| 4,946,449 A | 8/1990 | Davis, Jr. | |
| 4,954,126 A | 9/1990 | Wallsten | |
| 4,955,859 A | 9/1990 | Zilber | |
| 4,969,474 A | 11/1990 | Schwarz | |
| 4,973,301 A | 11/1990 | Nissenkorn | |
| 4,976,735 A | 12/1990 | Griffith et al. | |
| 4,978,341 A | 12/1990 | Niederhauser | |
| 4,994,019 A | 2/1991 | Fernandez et al. | |
| 4,994,066 A | 2/1991 | Voss | |
| 4,995,868 A | 2/1991 | Brazier | |
| 5,004,454 A | 4/1991 | Beyar et al. | |
| 5,007,898 A | 4/1991 | Rosenbluth et al. | |
| 5,012,822 A | 5/1991 | Schwarz | |
| 5,026,377 A | 6/1991 | Burton et al. | |
| 5,030,227 A | 7/1991 | Rosenbluth et al. | |
| 5,041,092 A | 8/1991 | Barwick | |
| 5,059,169 A | 10/1991 | Zilber | |
| 5,061,275 A | 10/1991 | Wallsten et al. | |
| 5,078,720 A | 1/1992 | Burton et al. | |
| 5,085,664 A | 2/1992 | Bozzo | |
| 5,096,454 A | 3/1992 | Samples | |
| 5,097,848 A | 3/1992 | Schwarz | |
| 5,112,306 A | 5/1992 | Burton et al. | |
| 5,116,309 A | 5/1992 | Coll | |
| 5,140,999 A | 8/1992 | Ardito | |
| 5,141,502 A | 8/1992 | Macaluso, Jr. | |
| 5,147,370 A | 9/1992 | McNamara et al. | |
| 5,167,614 A | 12/1992 | Tessmann et al. | |
| 5,176,664 A | 1/1993 | Weisman | |
| 5,188,596 A | 2/1993 | Condon et al. | |
| 5,207,672 A | 5/1993 | Roth et al. | |
| 5,209,725 A | 5/1993 | Roth | |
| 5,213,575 A | 5/1993 | Scotti | |
| 5,220,927 A | 6/1993 | Astrahan et al. | |
| 5,221,253 A | 6/1993 | Coll | |
| 5,224,953 A | 7/1993 | Morgentaler | |
| 5,246,445 A | 9/1993 | Yachia et al. | |
| 5,269,802 A | 12/1993 | Garber | |
| 5,282,472 A | 2/1994 | Companion et al. | |
| 5,300,022 A | 4/1994 | Klapper et al. | |
| 5,306,250 A | 4/1994 | March et al. | |
| 5,312,430 A | 5/1994 | Rosenbluth et al. | |
| 5,314,443 A | 5/1994 | Rudnick | |
| 5,322,501 A | 6/1994 | Mahmud-Durrani | |
| 5,344,435 A | 9/1994 | Turner et al. | |
| 5,346,467 A | 9/1994 | Coll | |
| 5,352,198 A | 10/1994 | Goldenberg et al. | |
| 5,354,263 A | 10/1994 | Coll | |
| 5,354,309 A | 10/1994 | Schnepp-Pesch et al. | |
| 5,356,423 A | 10/1994 | Tihon et al. | |
| 5,364,340 A | 11/1994 | Coll | |
| 5,366,506 A | 11/1994 | Davis | |
| 5,372,600 A | 12/1994 | Beyar et al. | |
| 5,380,268 A | 1/1995 | Wheeler | |
| 5,383,928 A | 1/1995 | Scott et al. | |
| 5,391,196 A | 2/1995 | Devonec | |
| 5,466,242 A | 11/1995 | Mori | |
| 5,487,740 A | 1/1996 | Sulek et al. | |
| 5,490,521 A | 2/1996 | Davis et al. | |
| 5,499,994 A | 3/1996 | Tihon et al. | |
| 5,512,032 A | 4/1996 | Kulisz et al. | |
| 5,514,176 A | 5/1996 | Bosley, Jr. | |
| 5,514,178 A | 5/1996 | Torchio | |
| 5,518,498 A | 5/1996 | Lindenberg et al. | |
| 5,520,697 A | 5/1996 | Lindenberg et al. | |
| 5,525,388 A | 6/1996 | Wand et al. | |
| 5,527,281 A | 6/1996 | Haas | |
| 5,527,336 A | 6/1996 | Rosenbluth et al. | |
| 5,540,713 A | 7/1996 | Schnepp-Pesch et al. | |
| 5,562,653 A | 10/1996 | Thompson | |
| 5,569,219 A | 10/1996 | Hakki et al. | |
| 5,588,965 A | 12/1996 | Burton et al. | |
| 5,601,537 A | 2/1997 | Frassica | |
| 5,609,583 A | 3/1997 | Hakki et al. | |
| 5,624,374 A | 4/1997 | Von Iderstein | |
| 5,624,395 A | 4/1997 | Mikhail et al. | |
| 5,624,410 A | 4/1997 | Tsukada et al. | |
| 5,667,486 A | 9/1997 | Mikulich et al. | |
| 5,667,522 A | 9/1997 | Flomenblit et al. | |
| 5,674,241 A | 10/1997 | Bley et al. | |
| 5,707,357 A | 1/1998 | Mikhail et al. | |
| 5,707,386 A | 1/1998 | Schnepp-Pesch et al. | |
| 5,711,314 A | 1/1998 | Ardito | |
| 5,713,877 A | 2/1998 | Davis | |
| 5,752,971 A | 5/1998 | Rosenbluth et al. | |
| 5,766,209 A * | 6/1998 | Devonec | 604/8 |
| 5,776,161 A | 7/1998 | Globerman | |
| 5,782,838 A | 7/1998 | Beyar et al. | |
| 5,782,916 A | 7/1998 | Pintauro et al. | |
| 5,792,400 A | 8/1998 | Talja et al. | |
| 5,817,102 A | 10/1998 | Johnson et al. | |
| 5,820,554 A | 10/1998 | Davis et al. | |
| 5,830,179 A | 11/1998 | Mikus et al. | |
| 5,833,707 A | 11/1998 | McIntyre et al. | |
| 5,836,951 A | 11/1998 | Rosenbluth et al. | |
| 5,860,999 A | 1/1999 | Schnepp-Pesch et al. | |
| 5,865,815 A | 2/1999 | Tihon | |
| 5,871,475 A | 2/1999 | Frassica | |
| 5,873,904 A | 2/1999 | Ragheb et al. | |
| 5,876,417 A | 3/1999 | Devonec et al. | |
| 5,906,575 A | 5/1999 | Conway et al. | |
| 5,911,732 A | 6/1999 | Hojeibane | |
| 5,916,195 A | 6/1999 | Eshel et al. | |
| 5,928,208 A | 7/1999 | Chu et al. | |
| 5,928,217 A | 7/1999 | Mikus et al. | |
| 5,931,860 A | 8/1999 | Reid et al. | |
| 5,964,732 A | 10/1999 | Willard | |
| 5,964,771 A | 10/1999 | Beyar et al. | |
| 5,971,967 A | 10/1999 | Willard | |
| 5,989,230 A | 11/1999 | Frassica | |
| 5,992,419 A | 11/1999 | Sterzer et al. | |
| 6,004,348 A | 12/1999 | Banas et al. | |
| 6,022,312 A | 2/2000 | Chaussy et al. | |
| 6,033,413 A | 3/2000 | Mikus et al. | |
| 6,047,216 A | 4/2000 | Carl et al. | |
| 6,053,897 A | 4/2000 | Sachse | |
| 6,056,775 A | 5/2000 | Borghi et al. | |
| 6,063,113 A | 5/2000 | Kavteladze et al. | |
| 6,066,168 A | 5/2000 | Lau et al. | |
| 6,119,045 A | 9/2000 | Bolmsjo | |
| 6,139,536 A | 10/2000 | Mikus et al. | |
| 6,187,037 B1 | 2/2001 | Satz | |
| 6,221,060 B1 | 4/2001 | Willard | |
| 6,223,086 B1 | 4/2001 | Carl et al. | |
| 6,226,553 B1 | 5/2001 | Carl et al. | |
| 6,230,060 B1 | 5/2001 | Mawhinney | |
| 6,289,249 B1 | 9/2001 | Arudlt et al. | |
| 6,366,818 B1 | 4/2002 | Bolmsjo | |
| 6,379,334 B1 | 4/2002 | Frassica | |
| 6,379,380 B1 | 4/2002 | Satz | |
| 6,383,217 B1 | 5/2002 | Satz | |
| 6,471,968 B1 | 10/2002 | Baker, Jr. et al. | |
| 6,477,426 B1 | 11/2002 | Fenn et al. | |
| 6,491,672 B2 | 12/2002 | Slepian et al. | |
| 6,494,879 B2 | 12/2002 | Lennox et al. | |
| 6,495,579 B1 | 12/2002 | Hunter | |

| | | | | | | |
|---|---|---|---|---|---|---|
| 6,496,736 | B1 | 12/2002 | Carl et al. | EP | 0 700 668 A1 | 3/1996 |
| 6,512,956 | B2 | 1/2003 | Arndt et al. | EP | 0 862 898 A2 | 6/1998 |
| 6,515,016 | B2 | 2/2003 | Hunter | EP | 0 935 977 A3 | 8/1999 |
| 6,527,702 | B2 | 3/2003 | Whalen et al. | JP | 5-177001 | 7/1993 |
| 6,530,951 | B1 | 3/2003 | Bates et al. | JP | 9-99058 | 4/1997 |
| 6,551,304 | B1 | 4/2003 | Whalen et al. | WO | WO 92/15361 | 9/1992 |
| 6,558,350 | B1 | 5/2003 | Hart et al. | WO | WO 94/18907 | 9/1994 |
| 6,589,228 | B2 | 7/2003 | Holzer | WO | WO 98/00192 | 1/1998 |
| 6,592,579 | B2 | 7/2003 | Arndt et al. | WO | WO 98/19713 | 5/1998 |
| 6,599,275 | B1 | 7/2003 | Fischer, Jr. | WO | WO 99/23952 | 5/1999 |
| 6,607,477 | B1 | 8/2003 | Longton et al. | | | |
| 6,675,050 | B2 | 1/2004 | Arndt et al. | | | |
| 6,682,555 | B2 | 1/2004 | Cioanta et al. | | | |
| 6,689,803 | B2 | 2/2004 | Hunter | | | |
| 6,716,252 | B2 | 4/2004 | Lazarovitz et al. | | | |
| 6,719,709 | B2 | 4/2004 | Whalen et al. | | | |
| 6,758,857 | B2 | 7/2004 | Cioanta et al. | | | |
| 6,759,431 | B2 | 7/2004 | Hunter et al. | | | |
| 6,770,101 | B2 | 8/2004 | Desmond, III et al. | | | |
| 6,788,977 | B2 | 9/2004 | Fenn et al. | | | |
| 6,794,363 | B2 | 9/2004 | Bejanin et al. | | | |
| 6,796,960 | B2 | 9/2004 | Cioanta et al. | | | |
| 6,802,846 | B2 | 10/2004 | Hauschild et al. | | | |
| 6,821,291 | B2 | 11/2004 | Bolea et al. | | | |
| 6,835,183 | B2 | 12/2004 | Lennox et al. | | | |
| 6,847,848 | B2 | 1/2005 | Sterzer et al. | | | |
| 6,893,430 | B2 * | 5/2005 | Eshel et al. ............ 604/544 | | | |
| 6,898,454 | B2 | 5/2005 | Atalar et al. | | | |
| 6,901,294 | B1 | 5/2005 | Whitehurst et al. | | | |
| 6,929,651 | B2 | 8/2005 | Huxel et al. | | | |
| 6,944,504 | B1 | 9/2005 | Arndt et al. | | | |
| 2002/0198506 | A1 | 12/2002 | Whalen et al. | | | |
| 2003/0036802 | A1 | 2/2003 | Lennox et al. | | | |
| 2003/0153807 | A1 | 8/2003 | Whalen et al. | | | |
| 2004/0015155 | A1 | 1/2004 | Whalen et al. | | | |
| 2005/0107721 | A1 | 5/2005 | Whalen et al. | | | |

FOREIGN PATENT DOCUMENTS

EP    0624342    11/1994

OTHER PUBLICATIONS

Albert, Joe, "Miltona company makes international impact", Mar. 19, 2004, www.echopress.com (3 pages).
"The Spanner Step by Step Guide", Jun. 30, 2005, www.abbeymoormedical.com (3 pages).
"The Spanner Specifications", Jun. 30, 2005, www.abbeymoormedical.com (1 page).
"Welcome to AbbeyMoor Medical, Inc.", The Spanner Prostatic Stent, Jun. 30, 2005, www.abbeymoormedical.com (2 pages).
Medical Policy, Medicine Section- Temporary Prostatic Stent, Jun. 30, 2005, www.regence.com (3 pages).
"AbbeyMoor Medical, Inc. Receives CE Mark Approval for The Spanner™ Temporary Prostatic Stent", Jul. 9, 2003, PRNewswire, www.forrelease.com (2 pages).
"Information about The Spanner Prostatic Stent", Jun. 30, 2005, www.abbeymoormedical.com (2 pages).
"A novel temporary prostatic stent for the relief of prostatic urethral obstruction", BJU International, Feb. 2004, www.abbeymoormedical.com (2 pages).
Corica, Alberto P., et al., "New Prostatic Stent for the Relief of Severe Lower Urinary Tract Symptoms", Poster #1471 AUA 2003 (1 page).
"The Spanner Temporary Prostatic Stent", Jun. 30, 2005, www.abbeymoormedical.com (3 pages).
Translation of Official Action by the Japanese Patent Office. Mailing date May 30, 2007, from Japanese patent application No. 2000-575444, which is related to U.S. Appl. No. 11/018,836 (4 pages).

* cited by examiner

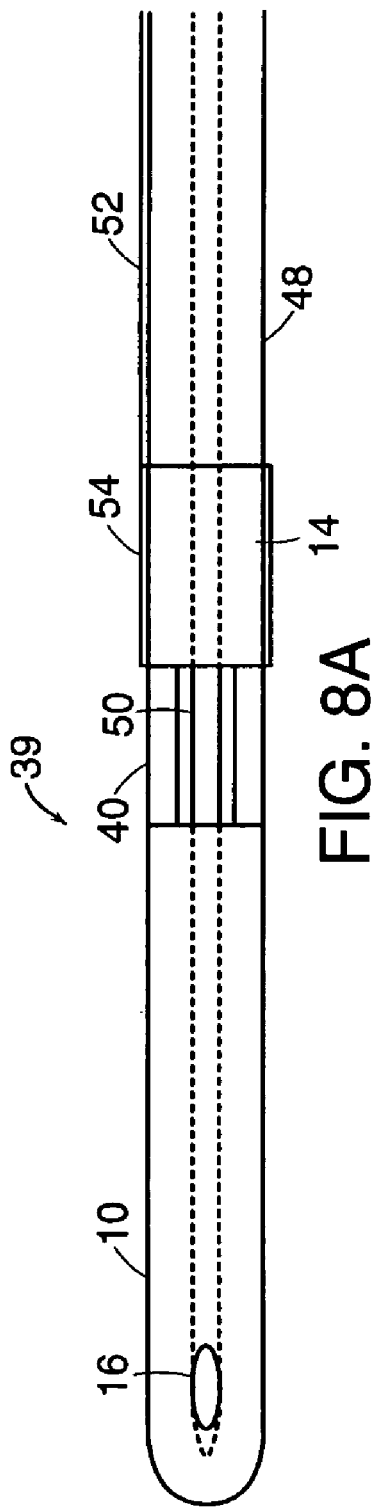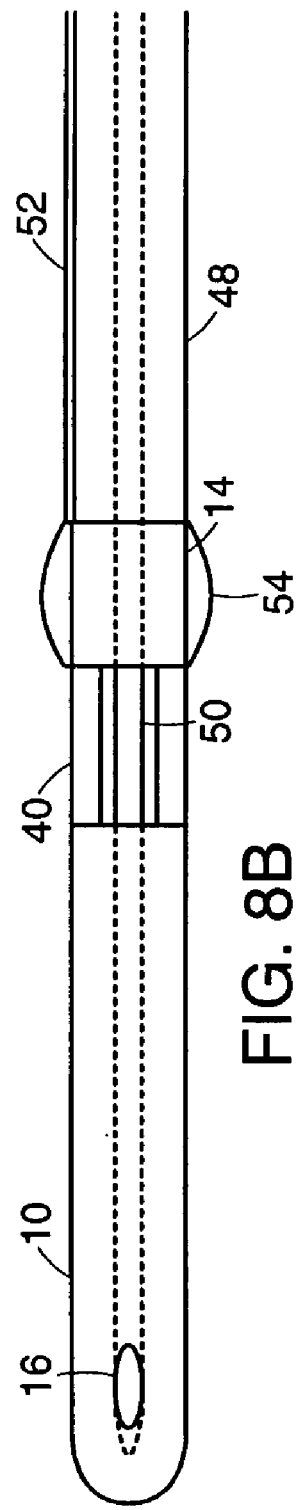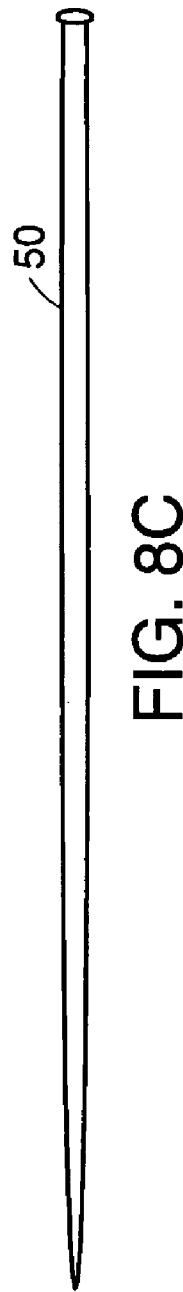

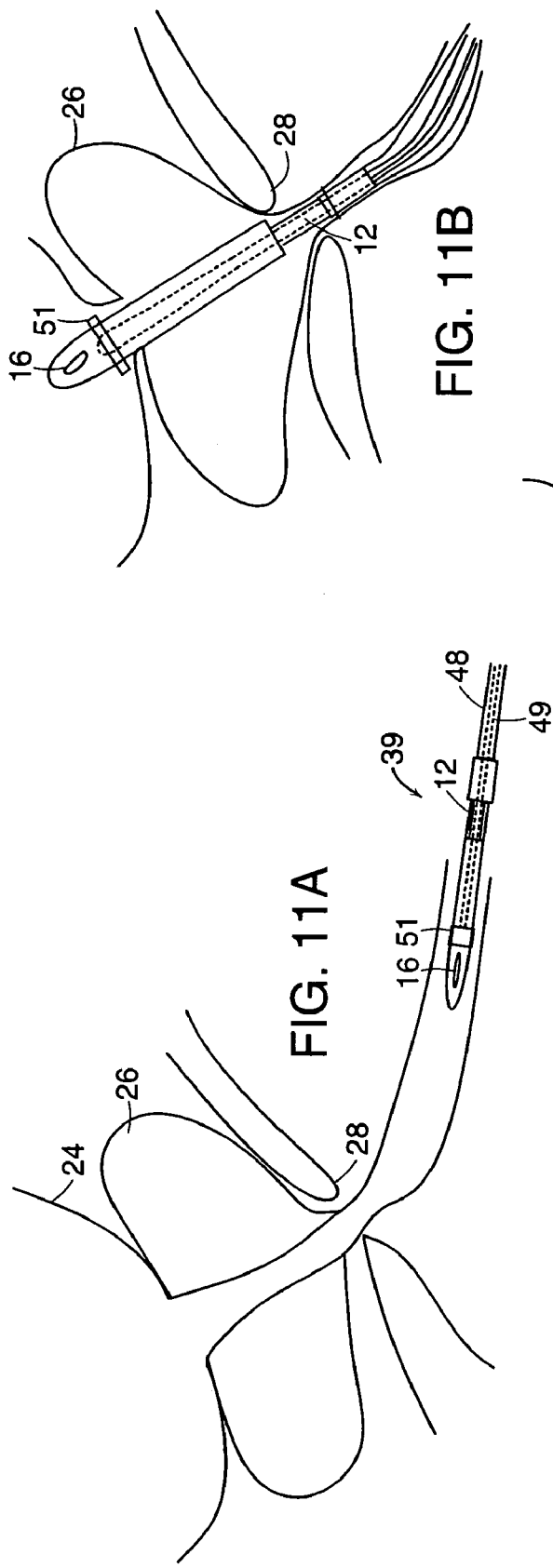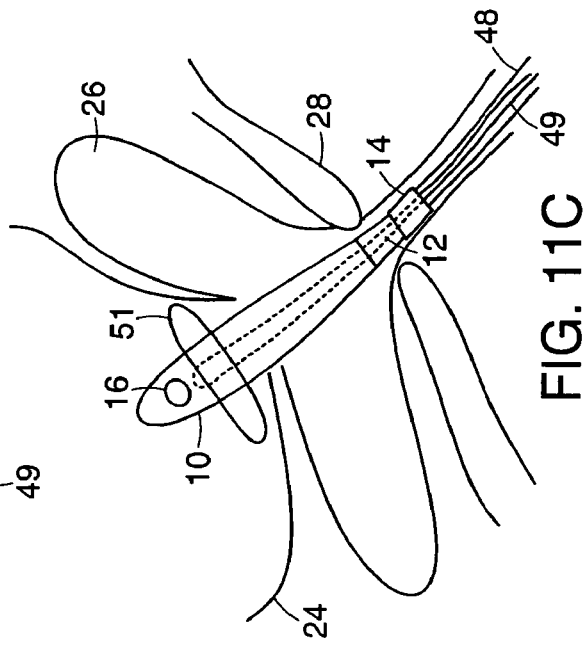

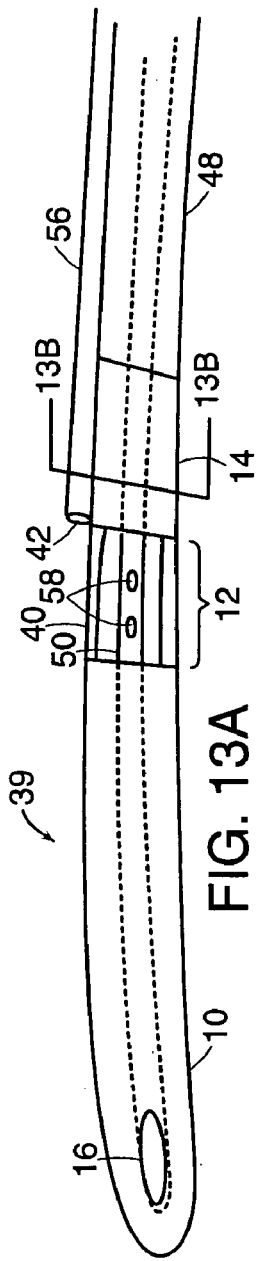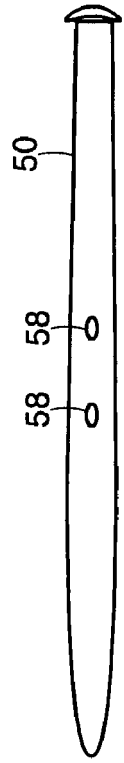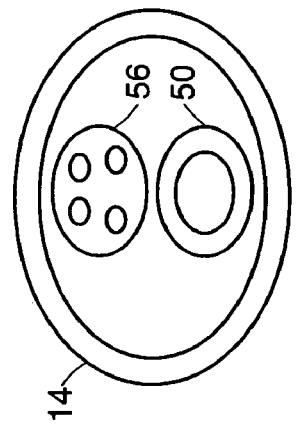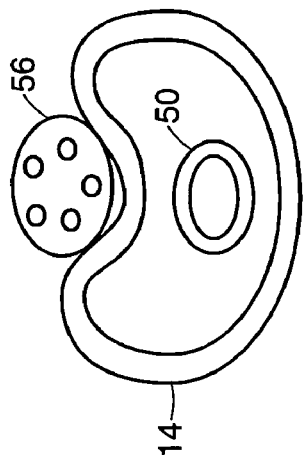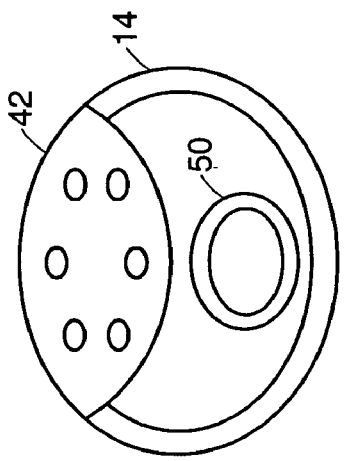

TREATING URINARY RETENTION

CROSS-REFERENCE TO RELATED APPLICATION

This is a continuation of U.S. application Ser. No. 10/260,483, filed on Sep. 30, 2002, to be U.S. Pat. No. 6,835,183 on Dec. 28, 2004, which is a continuation of U.S. application Ser. No. 09/313,563, filed on May 14, 1999, now U.S. Pat. No. 6,494,879, which incorporates by reference and claims priority to and the benefit of U.S. Provisional Patent Application No. 60/104,390, filed on Oct. 15, 1998.

TECHNICAL FIELD

The invention relates generally to urethral prostheses and methods of insertion into a body. More particularly, the invention relates to a urethral prosthesis having a bladder/prostate segment and a penile urethra segment connected by a bridge segment, which crosses the urinary sphincter.

BACKGROUND INFORMATION

Urinary retention in males is often caused by neurological disorders or by obstructions in the urinary tract. Neurogenic urinary retention is a condition in which a person is unable to empty his urinary bladder voluntarily due to a neurological dysfunction of the urinary bladder and/or of the urinary sphincter. Neurogenic urinary retention is due to an inability of the bladder to contract and/or of the urinary sphincter to relax. Patients with spinal cord injuries, multiple sclerosis, Parkinson's disease, or trauma to the pelvic region may suffer from neurogenic urinary retention on a permanent or transient basis.

Patients suffering from neurogenic urinary retention generally have limited options for draining their bladders. These include using a Foley catheter, intermittent catheterization, and a suprapubic drainage tube. All three options have high infection rates, are inconvenient for the patient and/or care giver, are uncomfortable for the patient, and cause the patient emotional distress.

Urinary retention is also caused by obstructions in the urethra, such as prostatic obstructions. The prostate gland encircles the urethra immediately below the urinary bladder. A common affliction among older males is benign prostatic hyperplasia (BPH), or the nonmalignant enlargement of the prostate. When the prostate becomes enlarged, it may restrict the urethra and thereby obstruct the flow of urine from the bladder.

A common treatment of BPH is surgical resection of the prostate and urethral tissue, but this option is not suitable for many patients. BPH afflicts primarily older males, so other health problems, such as cardiovascular disease, may prevent surgical intervention. Furthermore, potential complications associated with surgery, such as urinary infection, dysuria, and incontinence, may make a patient unwilling to undergo the surgery.

SUMMARY OF THE INVENTION

It is an object of the invention to relieve the symptoms of urinary retention in males without the high infection rates and other potential complications associated with current treatments. It is another object of the invention to provide a urethral prosthesis that resides within a bladder and urethra of a patient and that provides the patient control over drainage of the bladder without the discomfort and emotional distress associated with conventional treatments.

In one aspect, the invention relates to a urethral prosthesis including a first tubular element, a second tubular element, a bridge segment for joining the first and second tubular elements, and a valve. The first tubular element includes a distal portion with a drainage hole for receiving urine, a proximal end and a lumen, which extends from the drainage hole through the first tubular element to the proximal end of the first tubular element. At least a portion of the first tubular element is adapted for residing in a urethra of a patient. The second tubular element is adapted for residing in a penile urethra of a patient. The second tubular element includes a lumen extending from the bridge segment to its proximal end. The bridge segment has a diameter that is smaller than the diameter of the first tubular element and has a lumen for providing a permanent urine flow channel from the first tubular element through the urinary sphincter. The valve is disposed within the lumen of the second tubular element for controlling a flow of urine through the lumen of the second tubular element.

Embodiments according to this aspect of the invention can include the following additional features. The first and second tubular elements and the bridge segment may all be made of a pliable, biocompatible material, such as silicone rubber, for example. In another embodiment, the bridge segment comprises a spring disposed within the pliable, biocompatible material. In another embodiment, the proximal end of the second tubular element contains a suture wire to aid in removing the prosthesis from the urethra of a patient. The first and second tubular elements may also have an external surface coated with a coating including a plurality of gas bubbles therein.

In this aspect of the invention, the valve may be a magnetically-actuatable valve. In this embodiment, the valve includes a ferromagnetic valve seat, which has an aperture for the passage of fluid therethrough, and a valve element. The valve element includes a magnet encapsulated in a non-magnetic capsule. The capsule has a top portion and a base portion, which is wider than the top portion. The valve element is magnetically attracted to the valve seat so that it blocks the flow of fluid through the aperture in the valve seat.

In a second aspect, the invention relates to a urethral prosthesis including a first tubular element, a second tubular element, and a bridge segment of suture wires connecting the first and second tubular elements. The bridge segment resides within the urinary sphincter. The first tubular element has a drainage hole for receiving urine in its distal portion, a lumen extending from the drainage hole to its proximal end, and an external surface coated with a coating including a plurality of gas bubbles disposed therein. The first tubular element is adapted for residing at least partially in the urethra of a patient. The second tubular element is adapted for residing in a penile urethra of the patient and has a lumen.

Embodiments according to this aspect of the invention can include the following additional features. The second tubular element may also have an external surface coated with a coating including a plurality of gas bubbles. The first and second tubular elements may be composed of a pliable, biocompatible material, such as silicone rubber, for example. The second tubular element may include a suture wire attached to its proximal end to aid in removing the prosthesis from the patient. Finally, the second tubular element may include an optical lens embedded in its wall.

In a third aspect, the invention relates to a urethral prosthesis including a first tubular element, a second tubular element, and a bridge segment of suture wires connecting the first and second tubular elements. The bridge segment resides within the urinary sphincter. The first tubular element has a drainage hole for receiving urine in its distal portion, and a lumen extending from the drainage hole to its proximal end. The first tubular element is adapted for residing at least partially in the urethra of a patient. The second tubular element is adapted for residing in a penile urethra of the patient and has a lumen and includes an optical lens embedded in its wall.

Embodiments according to this aspect of the invention can include the following additional features. The first and second tubular element may also have an external surface coated with a coating including a plurality of gas bubbles. The first and second tubular elements may be composed of a pliable, biocompatible material, such as silicone rubber, for example. The second tubular element may include a suture wire attached to its proximal end to aid in removing the prosthesis from the patient.

The invention also relates to systems and methods for treating urinary retention. A system of the invention includes a urethral prosthesis of any of the above-described embodiments, an inflation cannula, and an inflatable balloon. The inflation cannula includes a lumen, which is in communication with the inflatable balloon for passage of fluid or gas to the balloon, so as to inflate the balloon. In one embodiment, the balloon covers at least a portion of the first tubular element when inflated. In another embodiment, the balloon covers the second tubular element when inflated.

A method of using such a system in which the balloon covers at least a portion of the first tubular element includes inserting the prosthesis in a urethra of a patient, pushing the prosthesis within the urethra so that the drainage hole is positioned in a bladder of the patient, delivering a volume of fluid or gas to the balloon through the inflation cannula so as to inflate the balloon, and withdrawing the prosthesis until a resistance is felt. This resistance indicates that the bridge segment of the prosthesis is positioned within the urinary sphincter.

A method of using such a system in which the balloon covers the second tubular element includes inserting the prosthesis in a urethra of a patient, pushing the prosthesis within the urethra until a first resistance is felt, delivering a volume of fluid or gas to the balloon through the inflation cannula so as to inflate the balloon, and pushing the prosthesis farther into the urethra until a second resistance is felt. This second resistance indicates that the bridge segment of the prosthesis is positioned within the urinary sphincter of the patient.

In an alternative embodiment of the method, the first and/or second tubular elements have an external surface coated with a coating including a plurality of gas bubbles. The method then further includes imaging the first and/or second tubular elements by ultrasound.

In alternative embodiments of the systems described above, a transducer is disposed within the balloon. A method of using such a system in which the balloon covers at least a portion of the first tubular element includes the steps of inserting the prosthesis in a urethra of a patient, pushing the prosthesis within the urethra so that the drainage hole is positioned in a bladder of the patient, delivering a volume of fluid or gas to the balloon through the inflation cannula so as to inflate the balloon, and withdrawing the prosthesis until a marked increase occurs in the pressure. This marked increase in pressure indicates that the bridge segment of the prosthesis is positioned within the urinary sphincter.

A method using such a system in which the balloon covers the second tubular element includes the steps of inserting the prosthesis within a urethra of a patient, pushing the prosthesis within the urethra until a first resistance is felt, delivering a volume of fluid to the balloon via the inflation cannula, monitoring a pressure of the balloon via the transducer, and pushing the prosthesis farther into the urethra until a marked increase occurs in the pressure. This marked increase indicates that the bridge segment is positioned within the urinary sphincter.

Methods of inserting a urethral prosthesis using such a system include inserting the urethral prosthesis into a urethra of the patient, pushing the prosthesis within the urethra until a first resistance is felt, delivering a volume of fluid via the inflation cannula to the inflatable balloon, so as to inflate the balloon, and pushing until a second resistance is felt. In an alternative embodiment, pressure in the balloon is monitored via a transducer, which is disposed within the balloon.

In an alternative embodiment of the above method, the first and/or second tubular elements have an external surface coated with a coating including a plurality of gas bubbles. The method then further includes imaging the first and/or second tubular elements by ultrasound. In an additional alternative embodiment, a transducer is inserted within the lumen of the second tubular element of the prosthesis for imaging the prosthesis by ultrasound and confirming that the bridge segment is properly positioned so that it spans the urinary sphincter. The ultrasound transducer may also be advanced into the lumen of the first tubular element after passing through the bridge segment, so as to confirm placement of the drainage hole in the bladder.

Another method of inserting a urethral prosthesis includes inserting a urethral prosthesis of any of the above-described embodiments into a urethra of a patient until the drainage hole of the first tubular element resides in the bladder and withdrawing the prosthesis until a resistance is felt. Embodiments of this method can include the following additional features. The external surface of the first and/or second tubular elements include an external surface coated with a coating including a plurality of gas bubbles. The method then further includes imaging the first and/or second tubular elements by ultrasound. In an additional alternative embodiment, a transducer is inserted within the lumen of the second tubular element of the prosthesis for imaging the prosthesis by ultrasound and confirming that the bridge segment is properly positioned so that it spans the urinary sphincter. The ultrasound transducer may also be advanced into the lumen of the first tubular element after passing through the bridge segment, so as to confirm placement of the drainage hole in the bladder.

Another method of inserting a urethral prosthesis includes inserting a urethral prosthesis of any of the above-described embodiments into a urethra of a patient and viewing the bridge segment of the prosthesis with an optical lens, so as to position the bridge segment within the urinary sphincter of the patient. In an alternative embodiment, the method also includes irrigating the urethra.

In other alternative embodiments of the method, the optical lens is an endoscope. The endoscope can be adapted for sliding within an external groove of the second tubular element. Also, the optical lens may be adapted for passing through the lumen of the second tubular element. Alternatively, the optical lens may be embedded within a wall of the second tubular element. Finally, the external surface of the first and/or second tubular elements include an external surface coated with a coating including a plurality of gas bubbles. The method then further includes imaging the first and/or second tubular elements by ultrasound. In an additional alternative embodiment, a transducer is inserted within the lumen of the second tubular element of the prosthesis for imaging the prosthesis by ultrasound and confirming that the bridge segment is properly positioned so that it spans the urinary sphincter. The ultrasound transducer may also be advanced into the lumen of the first tubular element after passing through the bridge segment, so as to confirm placement of the drainage hole in the bladder.

The foregoing and other objects., aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 8A is an illustration of a configuration for inserting a urethral prosthesis of the invention using an inflatable balloon that covers the second tubular element.

FIG. 8B is an illustration of the configuration of FIG. 8A in which the balloon is inflated.

FIG. 8C is an illustration of a positioning stylet for use in methods of the invention.

FIGS. 11A-11C are illustrations of a method of inserting a urethral prosthesis of the invention using a system of FIGS. 10A-10B.

FIG. 13A is an illustration of a configuration for inserting a urethral prosthesis of the invention using an endoscope.

FIG. 13B is a cross-sectional view, taken along line 13B-13B in FIG. 13A, of the urethral prosthesis which has an external groove for accommodating the endoscope.

FIG. 14 is an illustration of a positioning stylet having fluid delivery ports.

FIG. 15A is a cross-sectional view of a second tubular element of a urethral prosthesis of the invention having an optical lens embedded in its wall and a positioning stylet positioned within its lumen, such as the stylet of FIG. 14.

FIG. 15B is a cross-sectional view of a second tubular element of a urethral prosthesis of the invention having an endoscope and a positioning stylet positioned within its lumen.

DESCRIPTION

The invention relates to a urethral prosthesis for providing relief of urinary retention. A urethral prosthesis of the invention includes first and second tubular elements with an interposed bridge segment. The first and second tubular elements both have lumens extending therethrough. The bridge segment can be a generally non-compressible section with a diameter smaller than the diameter of each of the first and second tubular elements. Alternatively, the bridge segment can comprise at least one suture extending between the two tubular elements. A valve can be disposed in the lumen of the second tubular element, so as to control the flow of urine through the second tubular element.

When inserted into a patient, a drainage hole in the first tubular element resides within or near the patient's bladder, the remainder of the first tubular element resides within the prostatic urethra, the bridge segment passes through the urinary sphincter, and the second tubular element resides within the penile urethra. A urethral prosthesis of the invention therefore provides a channel for the flow of urine from the bladder out of the patient's body.

Systems and methods are also provided for the treatment of urinary retention using a urethral prosthesis, such as the types of prostheses described above. A system and method of the invention provides for the use of an inflatable balloon to locate the urinary sphincter and thereby ensure proper positioning of the urethral prosthesis of the invention. Other methods ensure proper positioning by detecting resistance or by viewing the urinary sphincter with an optical lens during insertion.

Figure 1:
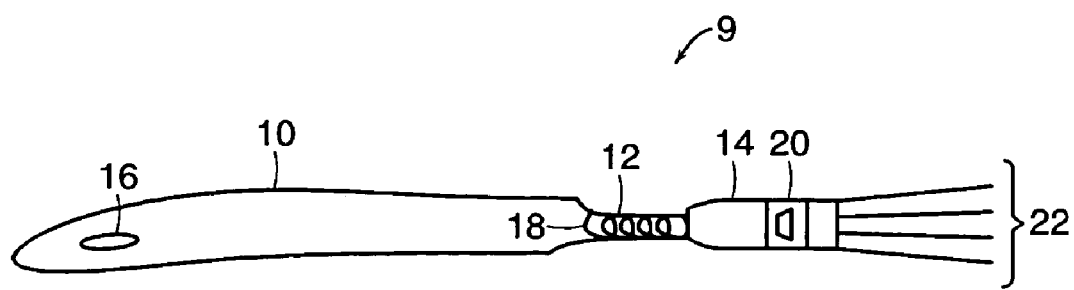
FIG. 1 is an illustration of an embodiment of a urethral prosthesis of the invention for use in treating neurogenic urinary retention.

An embodiment of a urethral prosthesis of the invention for use in treatment of neurogenic urinary retention is illustrated in FIG. 1. The prosthesis 9 includes a first tubular element 10, a bridge segment 12, and a second tubular element 14. The first tubular element 10 and the second tubular element 14 may be composed of any pliable biocompatible material, such as silicone rubber, for example. In one embodiment, the first tubular element 10 and the second tubular element 14 each has a lumen that is circular in cross-sectional shape. In an alternative embodiment, the lumen of the first tubular element 10 and the lumen of the second tubular element 14 are not circular in cross-sectional shape and may comprise a C-shape or a semi-circular shape, for example. The external surfaces of the first tubular element 10 and the second tubular 14 may be modified accordingly in order to create the non-circular shapes.

In some embodiments, the external surfaces of both the first tubular element 10 and the second tubular element 14 are coated with a plastic coating, such as a silicone coating, which is impregnated with gas bubbles. This coating makes the prosthesis echogenic, so that ultrasound may be used to ensure proper positioning of the prosthesis during insertion or to confirm proper placement of the prosthesis after it is inserted.

The first tubular element 10 and the second tubular element 14 both have lumens and are open at their proximal ends. The second tubular element 14 is also open at its distal end. The distal end of the first tubular element 10 is closed, but a drainage hole 16 is provided near the distal end. The bridge segment 12 has a reduced diameter as compared to the first tubular element 10 and the second tubular element 14. Disposed within the bridge segment 12 is a spring 18. The second tubular element 14 includes a valve 20 and suture wires 22. These suture wires 22 aid in removal of the prosthesis from the urethra of the patient. The prosthesis may be removed by pulling on suture wires 22. The suture wires 22 can be made of thin strands of a polymeric material, of silicone, metal, plastic, or rubber. The suture wires 22 may also be braided or monofilaments.

Figure 2:
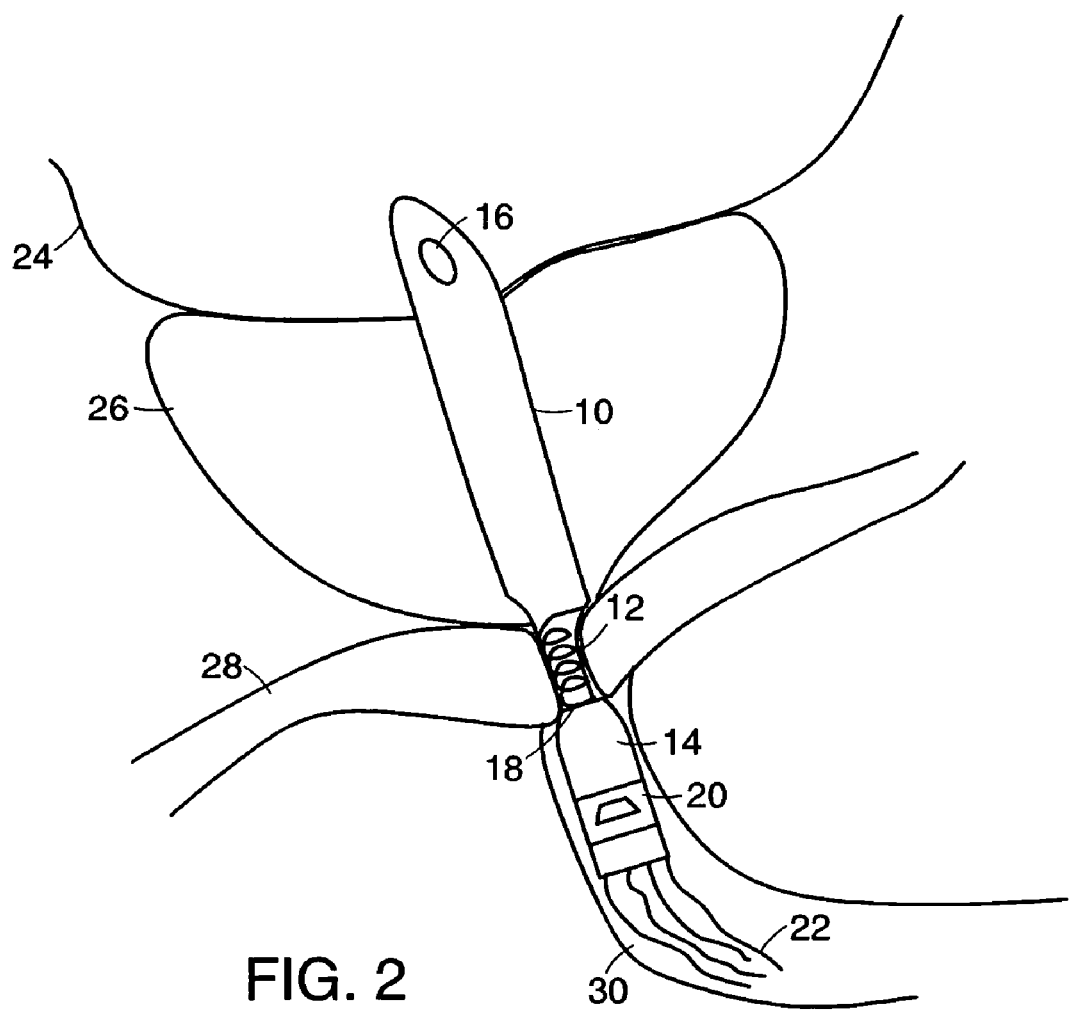
FIG. 2 shows the urethral prosthesis of FIG. 1 residing in a urethra of a patient.

The separate sections of the urethral prosthesis 9 shown in FIG. 1 are adapted for positioning within different segments of the urethra and the bladder. FIG. 2 is an illustration of the urethral prosthesis 9 in a urethra of a patient. The first tubular element 10 is inserted so that the drainage hole 16 resides within the bladder 24 of the patient. The remainder of the first tubular element 10 spans the prostatic urethra, which is identified as that portion of the urethra surrounded by the prostate 26. The bridge segment 12 spans the urinary sphincter 28, so as to provide a permanently open channel through which urine from the bladder can flow into the second tubular element 14, which resides in the penile urethra 30.

In one embodiment, the bridge segment 12 is non-compressible so as to hold the urinary sphincter in an open position and thereby provide a permanently open channel for the flow of urine from the bladder 24. The bridge segment 12 may be composed of any pliable biocompatible material, such as silicone rubber, for example. Patients suffering from neurogenic urinary retention are unable to control the opening and closing of the urinary sphincter and/or are unable to contract the bladder. By providing an open channel for the flow of urine across the urinary sphincter, these problems are alleviated. Furthermore, the bridge segment 12 includes the spring 18, which imparts flexibility to the bridge segment 12, thereby increasing the comfort level of the patient. The suture wires 22 extend into the penile urethra 30, where they may be grasped and pulled in order to remove the prosthesis 9 from the urethra of the patient.

Figure 3A:
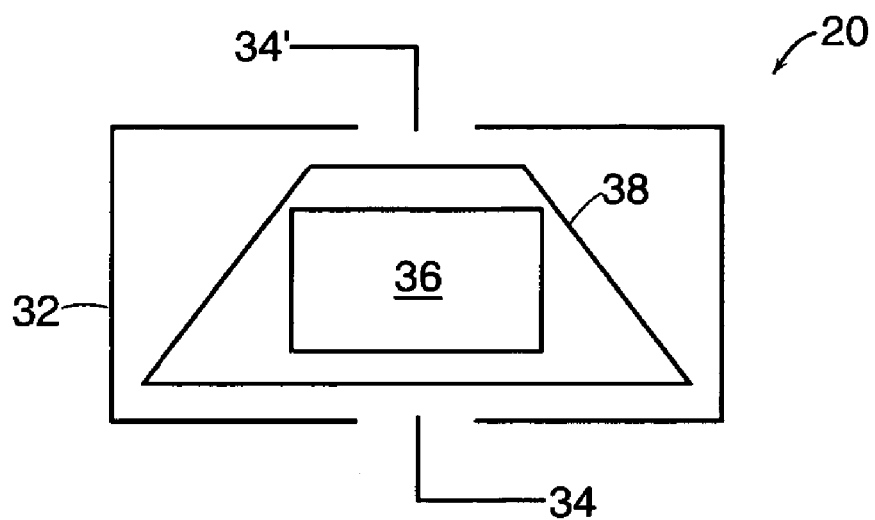
FIG. 3A is an illustration of a valve for use in a urethral prosthesis of the invention in its closed state.
Figure 3B:
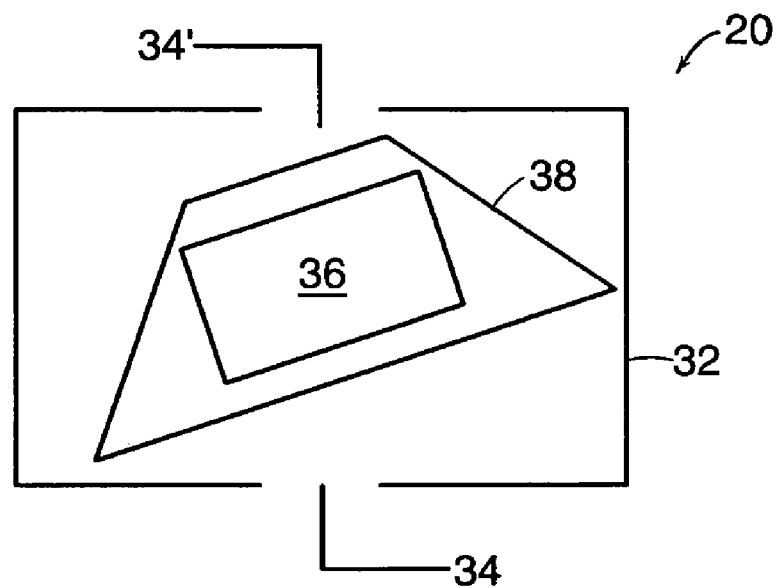
FIG. 3B is an illustration of a valve for use in a urethral prosthesis of the invention in its open state.

To control the flow of urine through the second tubular element 14 and out of the body, a valve 20 is disposed within the second tubular element 14. A suitable valve for use in a urethral prosthesis, as described above, is as described in U.S. Pat. No. 5,366,506, the entire disclosure of which is hereby incorporated by reference herein. In one embodiment, as shown in FIG. 3A, a valve includes a ferromagnetic valve seat 32, which includes apertures 34 and 34'. The valve 20 also includes a valve element 38, which includes a magnet 36. The walls of the valve element 38 are non-magnetic. As shown in FIG. 3A, the bottom portion of the valve element 38 is wider than the top portion of the valve element 38. Absent any external force, the valve element 38 is magnetically attracted to the valve seat 32, thereby blocking the aperture 34. The valve 20 is therefore in its closed position and fluid cannot flow through it. When an external magnetic force is applied to the valve 20, such as by contacting an exterior of a penis in which such a valve resides with a magnet, the valve element 38 is displaced so as to open the aperture 34, as is shown in FIG. 3B. In the open position, fluid flows into the valve 20 through the aperture 34' and then through the aperture 34 to the remainder of the penile urethra 30, and then out of the body.

Figure 4:
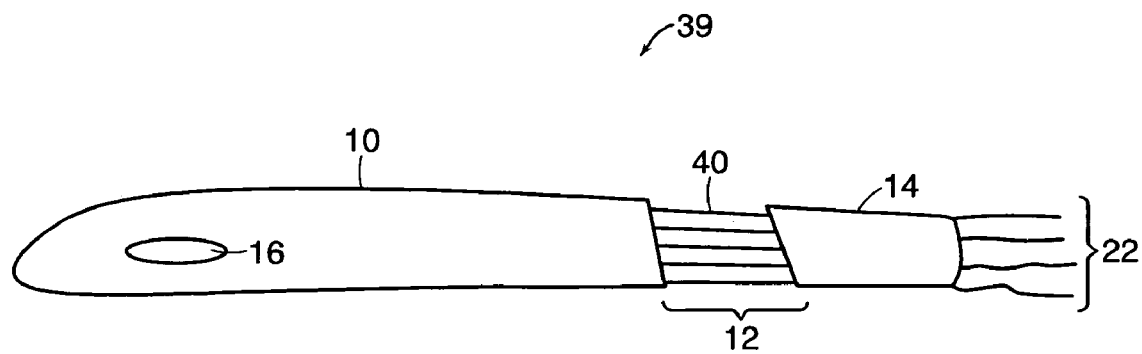
FIG. 4 is an illustration of an embodiment of a urethral prosthesis of the invention for use in treating urinary retention due to obstructions in the urethra.

An embodiment of a urethral prosthesis 39 of the invention for use in treating urinary retention due to an obstruction in the urethra is shown in FIG. 4. In this embodiment, the first tubular element 10 and the second tubular element 14 are as described above. The first tubular element. 10 has a closed distal end, except for a drainage hole 16. In this embodiment of the invention, the bridge segment 12 includes suture wires 40.

Figure 5:
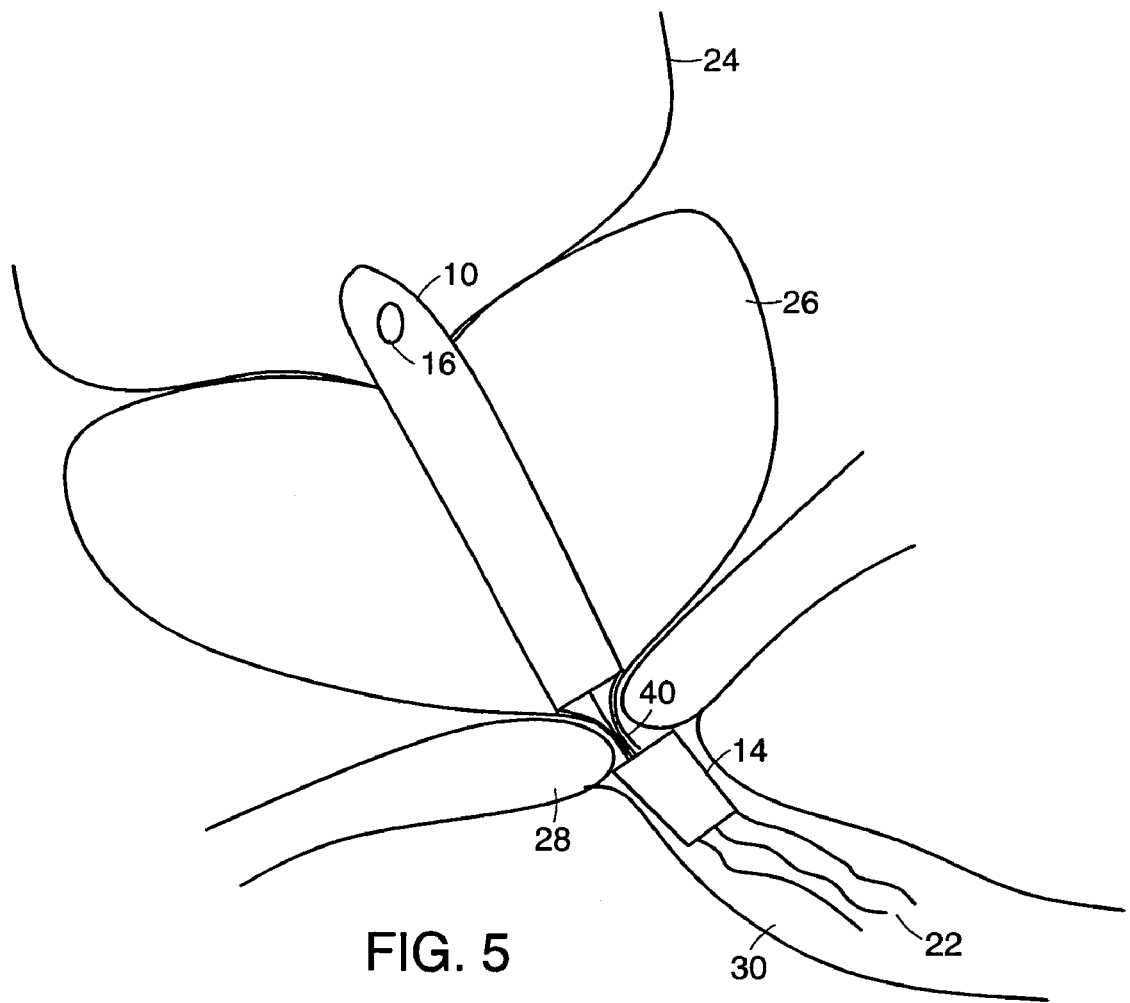
FIG. 5 shows a urethral prosthesis of FIG. 4 residing in a urethra of a patient.

In the case of urinary retention due to an obstruction in the urethra, patients have the ability to control their urinary sphincters and bladder contractions. A bridge segment that maintains a permanent flow channel is therefore not required. This embodiment of the invention therefore allows the patient to control the urinary sphincter, while the prosthesis otherwise maintains an open channel in the urethra. An illustration of a prosthesis 39 in a patient is shown in FIG. 5. Obstructions of the urethra commonly occur when the prostate 26 becomes enlarged and restricts the prostatic urethra, thereby blocking it. As can be seen in FIG. 5, the first tubular element 10 resides with its drainage hole 16 in the bladder 24, and with the remainder of the first tubular element 10 spanning the prostatic urethra. The first tubular element 10 therefore serves to maintain an open channel for the flow of urine through the prostatic urethra. When the urinary sphincter 28 is closed the suture wires 40 are compressed. When the urinary sphincter 28 is open, urine flows into the second tubular element 14 and through the penile urethra 30 to the exterior of the body.

In one embodiment of the urethral prosthesis 39, as shown in FIG. 4, the first tubular element 10 and the second tubular element 14 are composed of a pliable, biocompatible material, such as silicone rubber. In another embodiment, the first tubular element 10 and the second tubular element 14 have external surfaces coated with a plastic coating including a plurality of gas bubbles. As described above, this echogenic coating provides for ultrasound imaging of the device during or after insertion. The prosthesis 39 also contains suture wires 22, which aid in removing the prosthesis 39 from the patient, also as described above.

Figure 6:
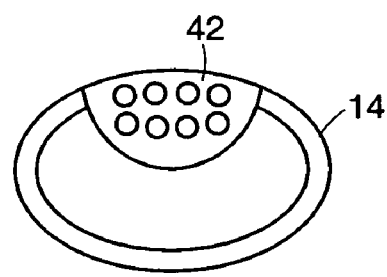
FIG. 6 is a cross-sectional view of a second tubular element of a prosthesis of the invention containing an optical lens embedded in its wall.

In an alternative embodiment of a urethral prosthesis for relieving urinary retention due to obstructions in the urethra, an optical lens is embedded within the wall of the second tubular element 14. FIG. 6 shows a cross-sectional view of a second tubular element 14 having an optical lens 42 embedded within its wall. The optical lens 42 may be used to ensure proper placement of the prosthesis during insertion. In one embodiment, the optical lens 42 is disposed at the distal end of the second tubular element 14, so that the urinary sphincter 28 may be viewed during the insertion procedure. (This insertion procedure is described in more detail below.) The first and second tubular elements of a urethral prosthesis containing an optical lens embedded within the wall of the second tubular element may or may not have external surfaces coated with an echogenic coating, as described above.

Figure 7:
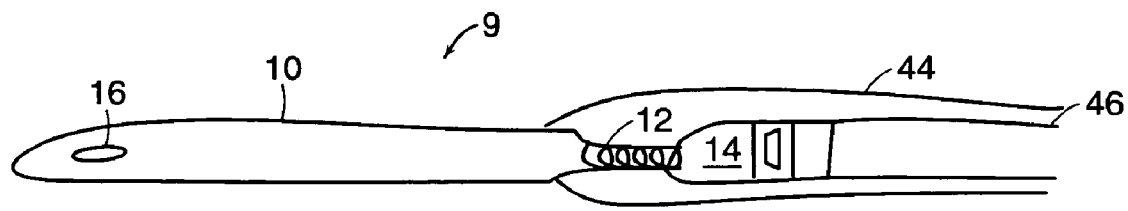
FIG. 7 is an illustration of a configuration for use in inserting a urethral prosthesis of the invention.

Methods of the invention relate to the insertion of a urethral prosthesis in a urethra and bladder of a patient. Methods the invention may include the use of any of the urethral prostheses described above. One such configuration for inserting a urethral prosthesis is shown in FIG. 7. The configuration in FIG. 7 includes the urethral prosthesis 9, the insertion sleeve 44, and the retractor 46. The insertion sleeve 44 is disposed over the second tubular element 14 and the bridge segment 12, and is partially disposed over the first tubular element 10. The retractor 46 is releasably attached to the proximal end of the second tubular element 14. The configuration of FIG. 7 is shown with the prosthesis 9 by way of example only. The kit may also be used in conjunction with the prosthesis 39, or any of the above-described embodiments of prostheses 9 and 39.

A method of insertion of a urethral prosthesis involves inserting the prosthesis 9, the insertion sleeve 44, and the retractor 46 into a urethra of a patient. The distal end of the first tubular element 10 is inserted first. The prosthesis 9 is inserted so that the drainage hole 16 resides in the bladder 24 of the patient, as shown in FIG. 2. If the first tubular element has an echogenic coating, the first tubular element 10 with the drainage hole 16 in the bladder 24 may be imaged with ultrasound, as described above. Alternatively, the placement of the prosthesis 9 may be imaged by inserting an ultrasound transducer into the lumen of the second tubular element 14. The ultrasound transducer may also be advanced through the bridge segment 12 of the prosthesis 9 and into the lumen of the first tubular element 10, so as to view the placement of the first tubular element within the bladder 24. The insertion sleeve 44 is then removed, and the retractor 46 is used to pull the prosthesis 9 back toward the opening of the urethra until a resistance is felt by the user. This resistance indicates that the bridge segment 12 is properly positioned in the urinary sphincter 28, as shown in FIG. 2. The retractor 46 is then disengaged from the second tubular element 14 and removed from the urethra. Proper positioning of the prosthesis may be confirmed with urethroscopy or ultrasound as described above.

A system of the invention is shown in FIGS. 8A-8C. The system contains the prosthesis 39, a pusher 48, a positioning stylet 50, an inflation cannula 52, and an inflatable balloon 54. The pusher 48 is sized and shaped for butting up against the proximal end of the second tubular element 14, so that it pushes against the second tubular element 14 and thereby advances the prosthesis 39 into a urethra of a patient. The pusher 48 has a lumen for insertion of the positioning stylet 50 therein. An illustration of the positioning stylet 50 is shown in FIG. 8C. The positioning stylet 50 is adapted to reside within the lumens of the pusher 48, the second tubular element 14, and the first tubular element 10, so as to maintain the prosthesis 39 in its extended position during the insertion procedure. Without the stylet 50, suture wires 40 may become bent, twisted, or collapsed during insertion.

The inflation cannula 52 of FIG. 8A also has a lumen, which is in communication with the inflatable balloon 54. To inflate the balloon 54, fluid or gas is delivered through the lumen of the inflation cannula 52. The balloon 54 is disposed over the second tubular element 14. In FIG. 8A, the balloon 54 is not inflated. FIG. 8B is an illustration of the system in which the balloon 54 is inflated over the second tubular element 14. The balloon 54 may be compliant or non-compliant. Balloons are standardized so that the injection of a known amount of fluid within the balloon induces inflation of the balloon to a specific diameter. Balloons may also be standardized with respect to diameter and pressure. Once the system of FIGS. 8A-8C is closed, a relation exists between the pressure within the system and the diameter of the balloon. The system is shown with the prosthesis 39 by way of example only. The system may also be used in conjunction with the prosthesis 9, or any of the above-described embodiments of prostheses 9 and 39.

Figure 9A:
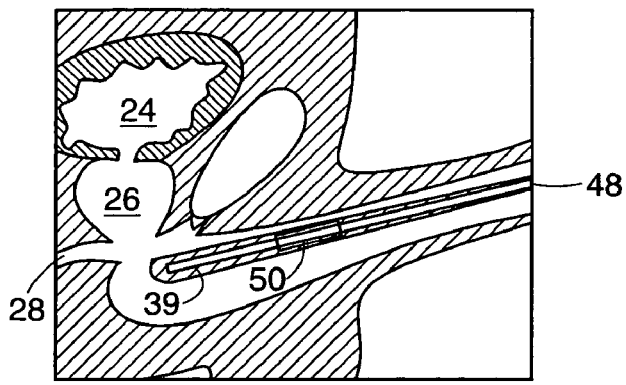
FIGS. 9A-9D are illustrations of a method of inserting a urethral prosthesis of the invention using a system of FIGS. 8A-8C.
Figure 9B:
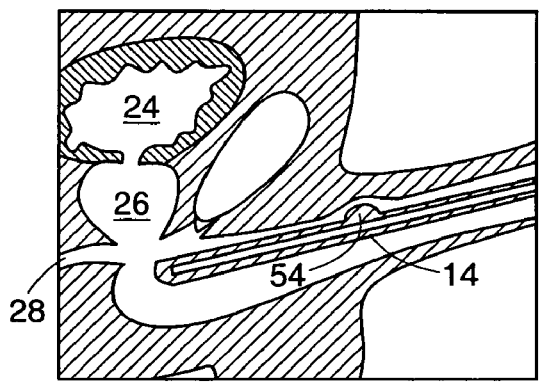
Figure 9C:
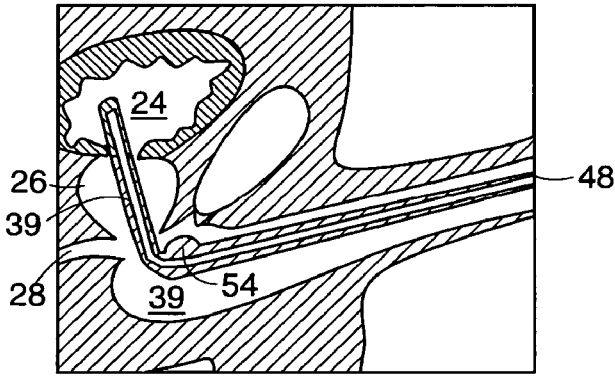

A method for inserting a prosthesis using the system shown in FIGS. 8A-8C is shown in FIGS. 9A-9D. In this method, the prosthesis 39, the positioning stylet 50, the pusher 48, the inflation cannula 52, and the balloon 54 are inserted into a urethra of a patient, with the distal end of the first tubular element 10 being inserted first. The prosthesis 39 is pushed by the pusher 48, along with the positioning stylet 50, until a first resistance is felt. This first resistance indicates that the distal end of the first tubular element 10 has contacted the urinary sphincter 28, as shown in FIG. 9A. The balloon 54 is then inflated by delivering fluid or gas via the inflation cannula 52 to the interior of the balloon 54. The balloon 54 inflates over the second tubular element 14, as shown in FIG. 9B. The prosthesis 39 is then pushed farther into the urethra until a second resistance is felt. This second resistance indicates that the balloon 54 has contacted the urinary sphincter 28, as shown in FIG. 9C. The pusher 48 and the inflation cannula 52 are removed from the urethra so as to deflate the balloon 54.

Figure 9D:
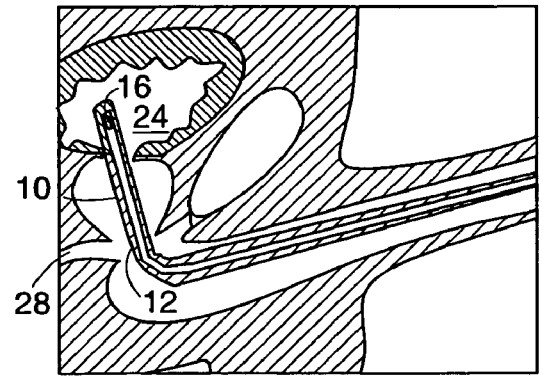

At this point, the prosthesis 39 is properly positioned within the urethra of the patient, such that the drainage hole 16 is residing in the bladder 24 and the bridge segment 12 spans the urinary sphincter 28, as shown in FIG. 9D. Proper placement of the prosthesis may be confirmed by urethroscopy or ultrasound, as described above.

Figure 10A:
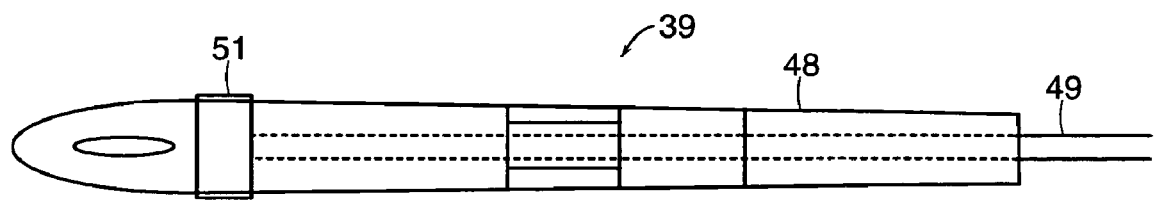
FIG. 10A is an illustration of a configuration for inserting a urethral prosthesis of the invention using an inflatable balloon that covers at least a portion of the first tubular element.
Figure 10B:
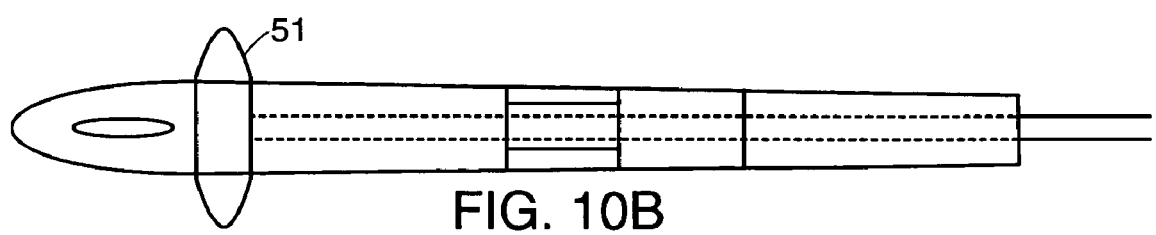
FIG. 10B is an illustration of the configuration of FIG. 10A in which the balloon is inflated.

An alternative system of the invention is shown in FIGS. 10A-10B. The system shown in FIG. 10A contains the prosthesis 39, a pusher 48, an inflation cannula 49, and an inflatable balloon 51. The pusher 48 is sized and shaped for butting up against the proximal end of the second tubular element 14, so that it pushes against the second tubular element 14 and thereby advances the prosthesis 39 into a urethra of a patient. The pusher 48 has a lumen for insertion of the inflation cannula 49 therein. The inflation cannula is adapted to reside within the lumens of the pusher 48, the second tubular element 14, and the first tubular element 10. The inflation cannula 49 also has a lumen, which is in communication with the inflatable balloon 51 so as to deliver a volume of fluid or gas to the balloon 51 and thereby inflate the balloon 51. As shown in FIG. 10B, the balloon 51 covers at least a portion of the first tubular element 10 when it is inflated. The balloon 51 is inflated at a position on the first tubular element 10 that resides in the bladder of a patient just above the prostate gland when inserted.

A method for inserting a prosthesis using the system shown in FIGS. 10A-10B is shown in FIGS. 11A-11C. In this method, the prosthesis 39, the pusher 48, the inflation cannula 49, and the balloon 51 are inserted into a urethra of a patient, with the distal end of the first tubular element 10 being inserted first, as shown in FIG. 11A. The prosthesis is pushed by the pusher 48, along with the inflation cannula 49, until the drainage hole 16 of the first tubular element 10 is positioned within the bladder 24, as shown in FIG. 11B. The balloon 51 is then inflated by delivering a volume of fluid or gas via the inflation cannula 49 to the interior of the balloon 51. The balloon 51 inflates over at least a portion of the first tubular element 10, as shown in FIG. 11C. The prosthesis 39 is then withdrawn (such as, for example, by using a retractor, as in FIG. 7) until a resistance is felt. This resistance indicates that the balloon 51 is contacting the opening 53 of the bladder 24 just above the prostate 26. This indicates that the prosthesis is properly positioned so that the bridge segment 12 spans the urinary sphincter 28. Proper placement of the prosthesis may be confirmed by urethroscopy or ultrasound, as described above.

Figure 12:
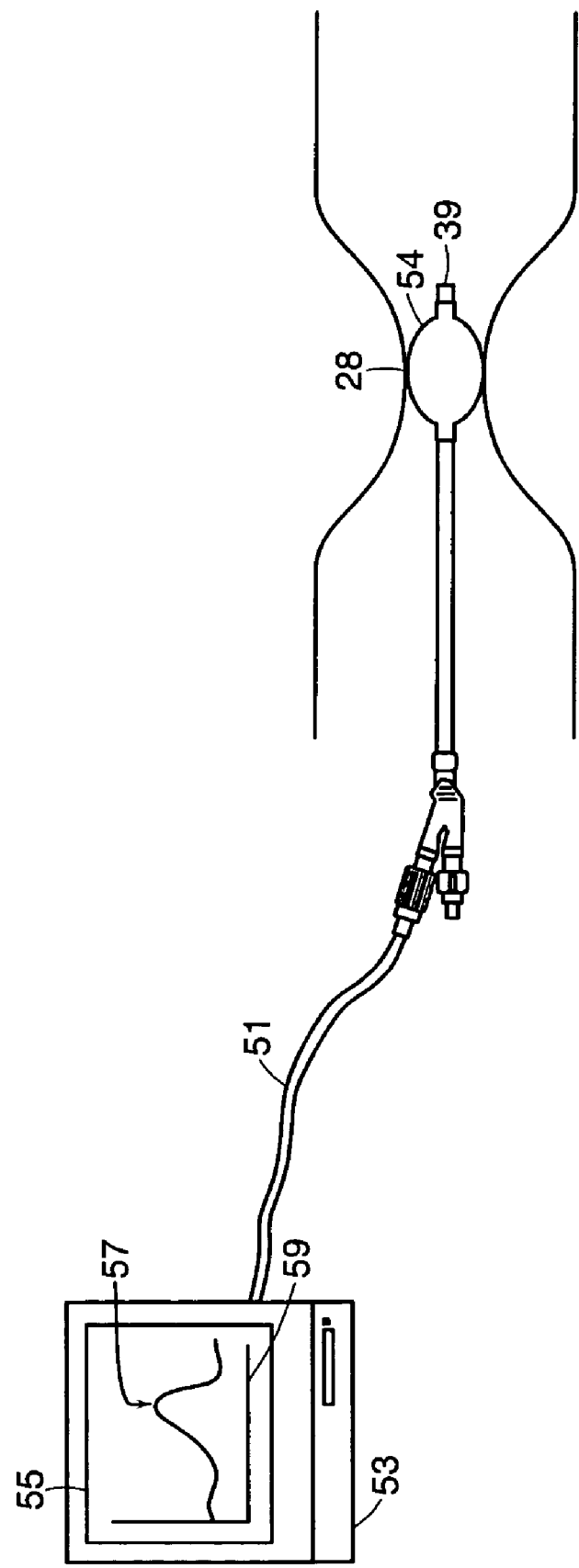
FIG. 12 is an illustration of a system for use in inserting a urethral prosthesis of the invention using a transducer to monitor changes in pressure of the balloon.

In an alternative embodiment of the system of FIGS. 8A-8C as shown in FIG. 12, a transducer (not shown) is disposed within the balloon 54. The location of the transducer within the closed system is unimportant as long as it is located within and senses changes in pressure within the area containing the fluid or gas. The transducer is in electrical communication via the connecting wire 51 with the controller 53. The controller 53 monitors variations in pressure. The controller 53 includes an indicator 55, which displays a plot 59 of the changes in pressure as a function of time or as a function of distance of insertion into the urethra. Indicator 55 may be a video monitor or a print-out display, for example. A marked increase in pressure 57, indicates that the balloon 54 has contacted the urinary sphincter 28. Detection of the location of the urinary sphincter 28 is then made by a visual reading of the plot 59, so as to ensure accurate placement of the prosthesis 39. Alternatively, when the balloon used is a compliant balloon, the plot 59 may be standardized to yield a defined pressure for a specific diameter for a known volume of inflation fluid. Alternatively, the embodiment of the system shown in FIGS. 10A-10B may be similarly adapted. For example, a transducer may be disposed within balloon 51 and may indicate placement of the prosthesis 39 by detecting marked increases in pressure as the prosthesis 39 is withdrawn from the urethra.

In an alternative embodiment, the system shown in FIG. 12 is used to measure the competency of the sphincter or detrusor muscles. This is accomplished by passing the balloon 54 with a known freestanding pressure-volume curve into the desired location and incrementally inflating it with known volumes of fluid. After each inflation of the balloon 54, a pressure measurement is taken and a pressure volume curve generated. By calculating the area difference between the curves, the net amount of work done by the sphincter is obtained.

In another alternative embodiment the system of FIG. 12 is used to determine adequate bulking pressures or volumes used during bulking procedures to remediate sphincter incontinence, for example. The system may be used to monitor the injection of agents typically used to bulk sphincters and create constrictions, such as to treat stress incontinence (AUS, Collagen products) or GERD. By placing a balloon 54 with the transducer in the desired position to be bulked, one can then monitor the compliance of the restriction created with the agent as it is injected. Clinical outcomes can be correlated to the compliance measured with this device to determine how much bulking agent is needed for the desired outcome.

The system of FIG. 12 may also have applications in urodynamic measurements, such as, compliance of body tissues within the urinary tract, arterial stenosis, aneurysm detection, or other areas where stricture, enlargement, or body tissue compliance quantification is pertinent.

Another configuration for insertion of a urethral prosthesis is shown in FIGS. 13A-13B. This configuration includes the prosthesis 39, the pusher 48, the positioning stylet 50, and an endoscope 56. The positioning stylet 50 has a lumen and contains fluid delivery ports 58, which are positioned to deliver fluid through the bridge segment 12 during the insertion procedure. Irrigating the insertion site during the insertion procedure is necessary to keep the optical lens 42 of the endoscope 56 clear for viewing. The positioning stylet 50 with delivery ports 58 is illustrated in FIG. 14.

In the configuration of FIGS. 13A-13B, the second tubular element 14 and the pusher 48 both have external grooves to allow the endoscope 56 to slide along the external surface of both the second tubular element 14 and the pusher 48. A cross-sectional view of the second tubular element 14 having an external groove is shown in FIG. 13B. As shown in FIG. 13B, the endoscope 56 fits within the external groove of the second tubular element 14. Also shown in the lumen of the second tubular element 14 is the positioning stylet 50. The configuration is shown with the prosthesis 39 by way of example only. The configuration may also be used in conjunction with the prosthesis 9, or any of the above-described embodiments of prostheses 9 and 39.

In alternative embodiments of this configuration, the optical lens 42 is embedded within the wall of the second tubular element 14, as shown in FIG. 15A. FIG. 15A is a cross-sectional view of the second tubular element 14. In this embodiment, the second tubular element 14 and the pusher 48 do not have external grooves. Also shown in FIG. 15A is the positioning stylet 50 within the lumen of the second tubular element 14. In another alternative embodiment, both the endoscope 56 and the positioning stylet 50 are adapted to fit within the lumen of the second tubular element 14, as shown in FIG. 15B.

A method of inserting a urethral prosthesis 39 using such a configuration include inserting the prosthesis 39, the pusher 48, the positioning stylet 50, and the endoscope 56 into a urethra of a patient. The distal end of the first tubular element 10 is inserted first, and the prosthesis 39 is advanced farther into the urethra by pushing against the proximal end of the second tubular element 14 with the pusher 48 and by pushing with the positioning stylet 50. While pushing the prosthesis 39 into the urethra, the endoscope 56 is used to view the bridge segment 12. In one embodiment, the urethra is irrigated by delivering a fluid through the lumen of the positioning stylet 50 and through the fluid delivery ports 58. The fluid may be any biological compatible fluid, such as saline, for example.

In this method of insertion, the bridge segment 12 is viewed with the endoscope 56 to determine when the bridge segment 12 is positioned such that it spans the urinary sphincter 28, as shown in FIG. 5. The positioning stylet 50, the pusher 48, and the endoscope 56 are then removed from the urethra. If the second tubular element 14 includes the optical lens 42 embedded within its wall, the method does not require use of the endoscope 56 for viewing. The bridge segment 12 is viewed with the embedded optical lens 42. Proper placement of the prosthesis may be confirmed by urethroscopy or ultrasound, as described above.

The above described systems and methods provide the patient control over the draining of the bladder. Urethral prostheses of the invention may also be used in situations where it is not desirable or possible for the patient to have control over the draining of the bladder. In such circumstances, the distal end of the first tubular element of the prosthesis may be open, and a catheter, such as a Foley catheter, for example, may be inserted through the lumens of the second tubular element, bridge segment, and first tubular element of the prosthesis. The catheter can then be attached to a urine collection bag and meter. This embodiment allows for the monitoring of urine production by the patient.

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

What is claimed is:

1. A urethral prosthesis, comprising:
    (a) a tubular element including a distal portion and a closed distal end, the distal portion defining a drainage hole for receiving urine from a bladder of a patient, the tubular element further including a proximal end and a lumen extending from the drainage hole through the tubular element to the proximal end, the tubular element further including an inflation balloon, the tubular element configured to maintain an open channel for fluid flow through a prostatic urethra of the patient when the prosthesis is positioned within the patient;
    (b) at least one suture extending from the proximal end of the tubular element, the at least one suture passing through a urinary sphincter of the patient when the prosthesis is positioned within the patient to allow the patient to control the urinary sphincter; and
    (c) a non-inflatable element extending from a proximal end of the at least one suture, the element including a proximal end and a distal end and defining a length between the proximal end and the distal end, the distal end of the element defining a width greater than a width of the proximal end of the element.

2. The urethral prosthesis of claim 1, wherein the inflation balloon disposed near the drainage hole.

3. The urethral prosthesis of claim 1, wherein the inflation balloon disposed on the tubular member.

4. The urethral prosthesis of claim 1, wherein the inflation balloon is inflatable over at least a portion of the tubular element.

5. The urethral prosthesis of claim 1, wherein the at least one suture comprises polymeric material.

6. The urethral prosthesis of claim 1, wherein the at least one suture comprises silicone.

7. The urethral prosthesis of claim 1, wherein the at least one suture comprises metal.

8. The urethral prosthesis of claim 1, wherein the at least one suture comprises plastic.

9. The urethral prosthesis of claim 1, wherein the at least one suture comprises rubber.

10. The urethral prosthesis of claim 1, wherein the at least one suture comprises braided filaments.

11. The urethral prosthesis of claim 1, wherein the at least one suture comprises a monofilament.

12. The urethral prosthesis of claim 1, wherein the tubular element comprises a pliable, biocompatible material.

13. The urethral prosthesis of claim 1, wherein the tubular element includes a silicone coating.

14. The urethral prosthesis of claim 1, wherein the tubular element comprises silicone rubber.

15. The urethral prosthesis of claim 1, wherein the tubular element comprises a circular cross section.

16. The urethral prosthesis of claim 1, wherein the tubular element comprises a C-shaped cross section.

17. The urethral prosthesis of claim 1, wherein the tubular element comprises a semi-circular cross section.

18. The urethral prosthesis of claim 1, wherein the element comprises a pliable, biocompatible material.

19. The urethral prosthesis of claim 1, wherein the element includes a silicone coating.

20. The urethral prosthesis of claim 1, wherein the element comprises silicone rubber.

21. The urethral prosthesis of claim 1, wherein at least a portion of the element comprises a tubular shape.

22. The urethral prosthesis of claim 1, wherein the element comprises a circular cross section.

23. The urethral prosthesis of claim 1, wherein the element comprises a C-shaped cross section.

24. The urethral prosthesis of claim 1, wherein the element comprises a semi-circular cross section.

25. The urethral prosthesis of claim 1, further comprising at least one removal suture.

26. The urethral prosthesis of claim 25, wherein the at least one removal suture is connected to the tubular element.

27. The urethral prosthesis of claim 25, wherein the at least one removal suture is connected to the element.

28. The urethral prosthesis of claim 25, wherein the at least one removal suture comprises polymeric material.

29. The urethral prosthesis of claim 25, wherein the at least one removal suture comprises silicone.

30. The urethral prosthesis of claim 25, wherein the at least one removal suture comprises metal.

31. The urethral prosthesis of claim 25, where wherein the at least one removal suture comprises plastic.

32. The urethral prosthesis of claim 25, wherein the at least one removal suture comprises rubber.

33. The urethral prosthesis of claim 25, wherein the at least one removal suture comprises braided filaments.

34. The urethral prosthesis of claim 25, wherein the at least one removal suture comprises a monofilament.

35. The urethral prosthesis of claim 1, wherein the tubular element has a length greater than the length of the element.

36. The urethral prosthesis of claim 1, wherein the distal end of the element has an outer diameter greater than an outer diameter of the proximal end of the element.

37. The urethral prosthesis of claim 1, wherein the element is configured to be disposed within a penile urethra.

38. The urethral prosthesis of claim 1, wherein the element is configured to substantially maintain the width at the distal end and the width at the proximal end during both insertion and while maintained within a urethra.

* * * * *